United States Patent [19]

Patel et al.

[11] Patent Number: 4,752,605

[45] Date of Patent: Jun. 21, 1988

[54] 7-CHLORO-4A-HYDROXY-8-METHOX-YTETRACYCLINE, ANTIBIOTIC COMPOSITIONS CONTAINING THEM AND A METHOD OF USING

[75] Inventors: Mahesh G. Patel, Verona; Ann C. Horan, Summit; Joseph A. Marquez, Montclair; George H. Miller, Montville, all of N.J.; Richard W. Vaughan, Augusta, Ga.

[73] Assignee: Schering Corporation, Kenilworth, N.J.

[21] Appl. No.: 764,275

[22] Filed: Aug. 9, 1985

[51] Int. Cl.[4] .................... C07C 103/19; A61K 31/65
[52] U.S. Cl. ................... 514/152; 260/351.3; 435/64; 435/822
[58] Field of Search ............ 260/351.3; 514/152; 435/64, 822

[56] References Cited

U.S. PATENT DOCUMENTS 3,201,424  8/1965  McCormick et al. ............ 260/351
3,226,305  12/1965  McCormick et al. ............ 435/64
3,360,559  12/1967  McCormick et al. ............ 260/569
3,462,487  8/1969  Kinney et al. ................. 435/64 X
4,156,723  5/1979  Hauck et al. ................. 564/173 X

FOREIGN PATENT DOCUMENTS 1553651  12/1968  France .
373375  1/1964  Switzerland .

OTHER PUBLICATIONS

Nickers et al., *Organic Chemistry* (1977), pp. 275–277.
Weber et al., Fenkalblatt for Bakteriologie, Mikrabiologie und Hygiene Abt. 1, Supplemente 11, 1981, pp. 465–468.

*Primary Examiner*—Floyd D. Higel
*Assistant Examiner*—Carolyn S. Greason
*Attorney, Agent, or Firm*—Thomas D. Hoffman; Gerald S. Rosen

[57] ABSTRACT

The antibiotic 7273 complex is elaborated by the microorganism, *Dactylosporangium vescum* ATCC 39499. The novel 7-chloro-4a-hydroxy-8-methoxytetracycline isolated from antibiotic 7273 complex is active against gram-positive and gram-negative aerobes.

9 Claims, 4 Drawing Sheets

7-CHLORO-4A-HYDROXY-8-METHOXYTETRA- CYCLINE, ANTIBIOTIC COMPOSITIONS CONTAINING THEM AND A METHOD OF USING

BACKGROUND

This invention relates to a new tetracycline antibiotic, 7-chloro-4a-hydroxy-8-methoxytetracycline, isolated from an antibiotic complex designated as antibiotic 7273 complex which is produced by fermentation under controlled conditions using a biologically pure culture of the new microorganism *Dactylosporangium. vescum* ATCC 39499.

In a related, commonly-assigned, co-pending application Ser. No. 763,400, filed on even date herewith, another new tetracycline, 7-chloro-8-methoxytetracycline, produced by fermentation of mutants of *A. brunnea, A. brunnea* var. *antibiotica* var. nov., ATCC 53108 and ATCC 53180 is disclosed.

In another related, commonly-assigned, copending application Ser. No. 763,742, filed on even date herewith, another new tetracycline, 7-chloro-8-methoxy 2'-N-methyltetracycline, produced by fermentation of *Actinomadura brunnea* ATCC 39216 is disclosed.

SUMMARY OF INVENTION

The present invention embraces the biologically pure culture of the microorganism *Dactylosporangium vescum* having the identifying characteristics of ATCC 39499 as well as mutants and variants thereof, said culture being capable of producing antibiotic 7273 complex comprising the antibiotic compound of this invention, 7-chloro-4a-hydroxy-8-methoxytetracycline in a recoverable quantity upon fermentation under aerobic conditions in an aqueous medium containing assimilable sources of nitrogen and carbon.

The present invention is also directed to novel antibiotic 7273 complex and to one component thereof, namely, 7-chloro-4a-hydroxy-8-methoxytetracycline, a compound represented by the formula

[Chemical structure]

or a pharmaceutically acceptable salt thereof.

The compound of this invention is systematically named 7-chloro-4-dimethylamino-8-methoxy-1,4,4a,5-,5a,6,11,12a-octahydro-3,4a,6,10,12,12a-hexahydroxy-6-methyl-1,11-dioxo-2-naphthacene carboxamide or simply 7-chloro-4a-hydroxy-8-methoxytetracycline.

The present invention in addition is also directed to a pharmaceutical composition comprising an antibiotically effective amount of 7-chloro-4a-hydroxy-8-methoxytetracycline or a pharmaceutically acceptable salt thereof and a pharmaceutically acceptable carrier or diluent.

The present invention in addition is directed to a method of eliciting an antibiotic effect in a host, e.g. a mammal, having a susceptible infection which comprises administering to said host an antibiotically effective amount of the compound of this invention, 7-chloro-4a-hydroxy-8-methoxytetracycline, or a pharmaceutical composition thereof.

ISOLATION AND PURIFICATION OF THE ANTIBIOTIC 7273 COMPLEX

Antibiotic 7273 complex is produced when the elaborating organism, *Dactylosporangium vescum* having the identifying characteristics of ATCC 39499 is grown in an appropriate nutrient medium.

Antibiotic 7273 complex may be isolated from the fermentation broth by solvent extraction and filtration, and by employing the following procedure:

(a) Adjust the pH of the whole broth to 4;

(b) Extract the whole broth using two volumes of organic solvent (e.g. ethyl acetate) each time for each volume of broth;

(c) Combine the organic solvent extracts and remove the organic solvent by stripping to yield a solid residue;

(d) Dissolve the residue in acetone and filter off the insolubles;

(e) Add a mixture of 1:4 (v/v) ethyl ether: hexane to the filtrate until a precipitate forms; and (f) Collect the precipitate.

Using the above procedure, 12.5 g of antibiotic 7273 complex were obtained from 80 L of fermentation broth. Since the antibiotic 7273 complex is made up of at least two dissimilar components, no meaningful physico-chemical data can be determined for the complex.

SEPARATION OF THE ANTIBIOTIC 7273 COMPLEX

The antibiotic 7273 complex is made up of at least two active components, one of which has been isolated and characterized as the novel 4a-,8-substituted chlortetracycline of this invention, 7-chloro-4a-hydroxy-8-methoxytetracycline.

The active antibiotics, including 7-chloro-4a-hydroxy-8-methoxytetracycline can be isolated from the antibiotic 7273 complex (as the HCl salt) by chromatography using, for example, a Sephadex G-25 gel column. The eluate (dilute aqueous HCl) from the column was monitored by determining the activity of each fraction against *S. aureus* and *E. coli*. The desired active fractions were combined and lyophilized to give 7-chloro-4a-hydroxy-8-methoxytetracyline as a light yellow powder.

The physical and spectroscopic data for 7-chloro-4a-hydroxy-8-methoxytetracycline are presented in Table I below.

TABLE I

Physico-Chemical Data for 7-Chloro-4a-Hydroxy-8-Methoxytetracycline (a) The data for the chemical analysis are the

TABLE I-continued

Physico-Chemical Data for 7-Chloro-4a-Hydroxy-8-Methoxytetracycline following:
Calc'd for: $C_{23}H_{25}O_{10}N_2Cl\cdot HCl$

| Found: | C | 49.3 | H | 4.68 | N | 5.00 | Cl | 12.5 |
|---|---|---|---|---|---|---|---|---|
|  | C | 46.1 | H | 4.58 | N | 4.52 | Cl | 11.7 |

(b) The Fast Atom Bombardment (FAB) yielded an $M^+$ peak at 525.1273. This corresponds to the formula $C_{23}H_{25}N_2O_{10}Cl + H$ which calculates for the exact mass, 525.1276.

(c) The ultraviolet absorption maxima in methanol are: 234 ($\epsilon$16,750), 258 ($\epsilon$15,500), and 372 nm ($\epsilon$18,000). The ultraviolet absorption maxima shift to 233 ($\epsilon$15,500), 258 ($\epsilon$16,800), and 368 nm ($\epsilon$17,200) upon the addition of acid. The ultraviolet maxima shift to 240 ($\epsilon$18,800), 280 ($\epsilon$16,400) and 381 nm ($\epsilon$17,700) upon the addition of base.

Figure 1:
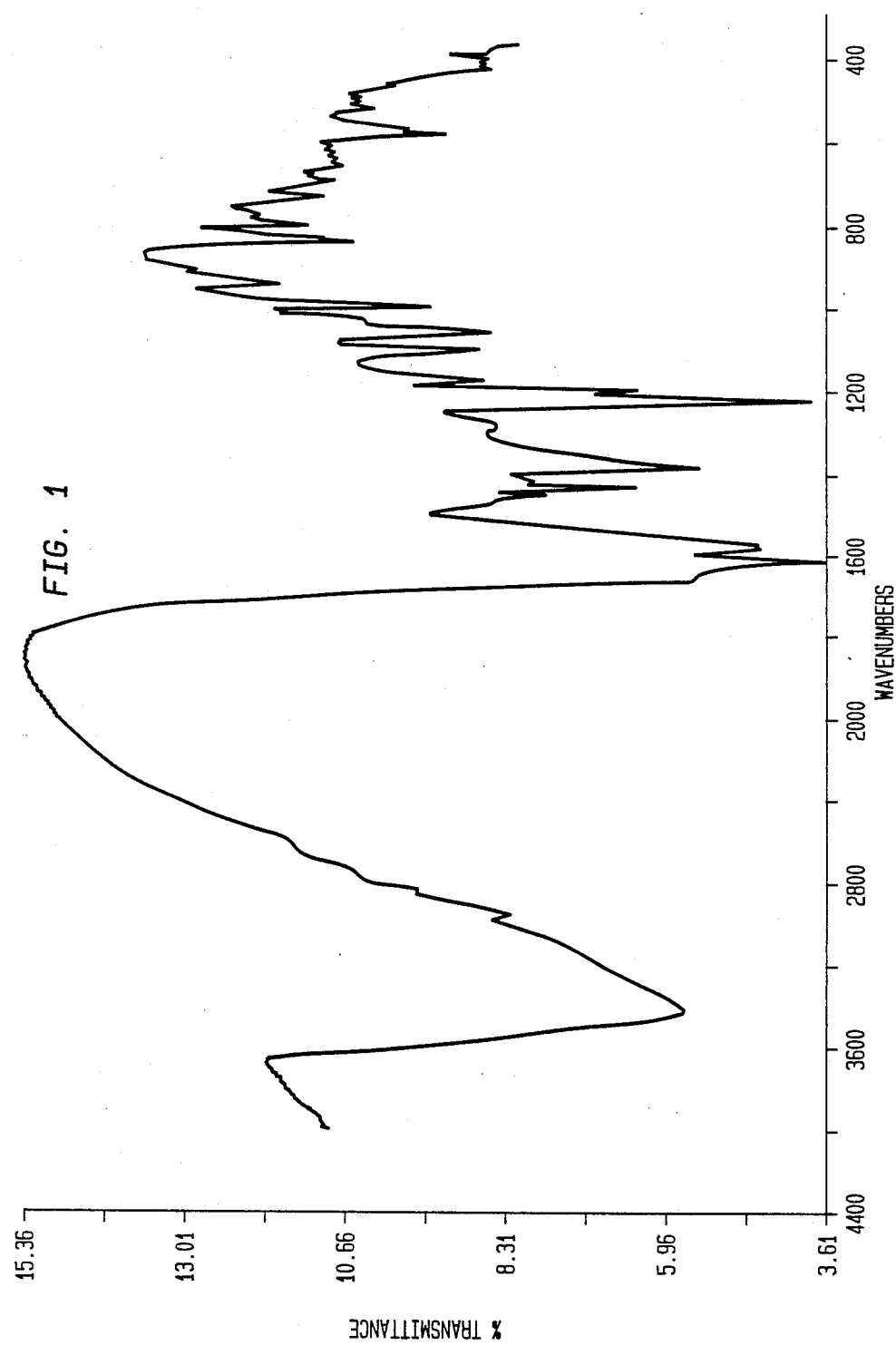
FIG. 1 is the infrared spectrum of 7-chloro-4a-hydroxy-8-methoxytetracycline in KBr.

(d) The infrared spectrum in KBr is shown in FIG. 1. The characteristic absorption bands are the following: 3400 (br), 1611, 1570, 1558, 1461, 1433, 1414, 1380, 1309, 1240, and 1209 $cm^{-1}$.

Figure 2:
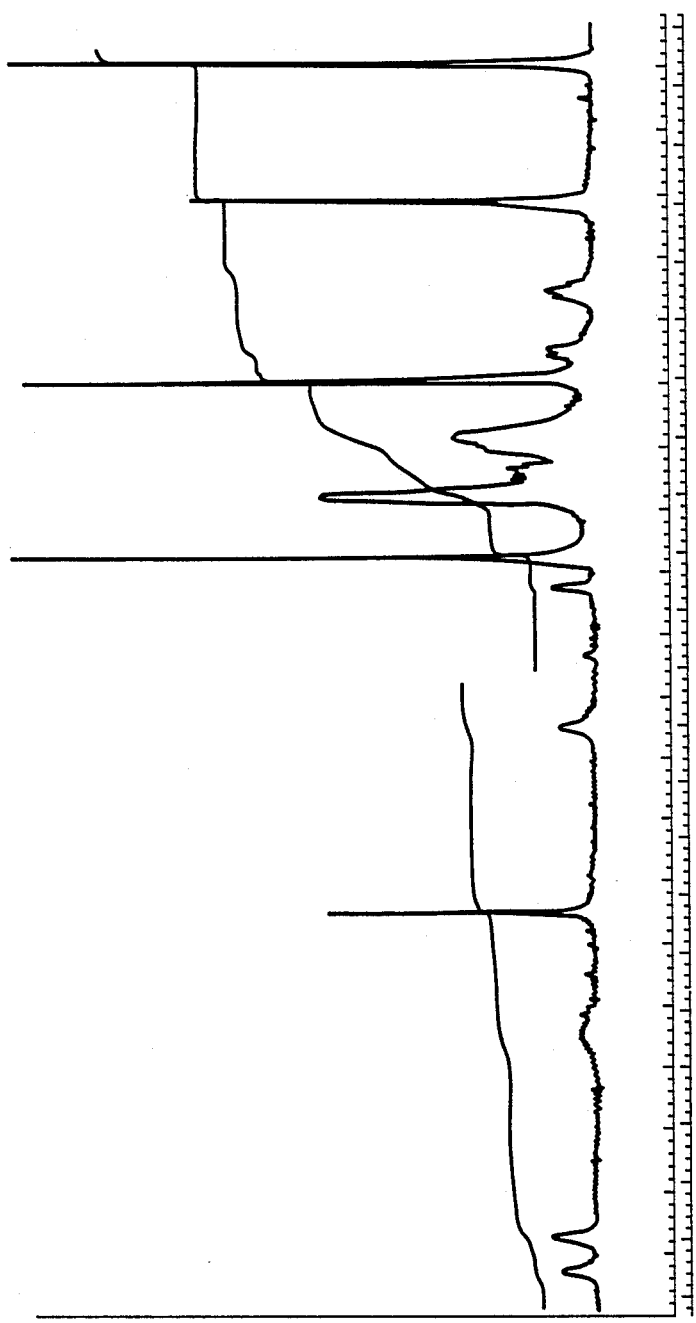
FIG. 2 the $^1$H NMR spectrum of 7-chloro-4a-hydroxy-8-methoxytetracycline in dimethyl sulfoxide-$d_6$.
Figure 3:
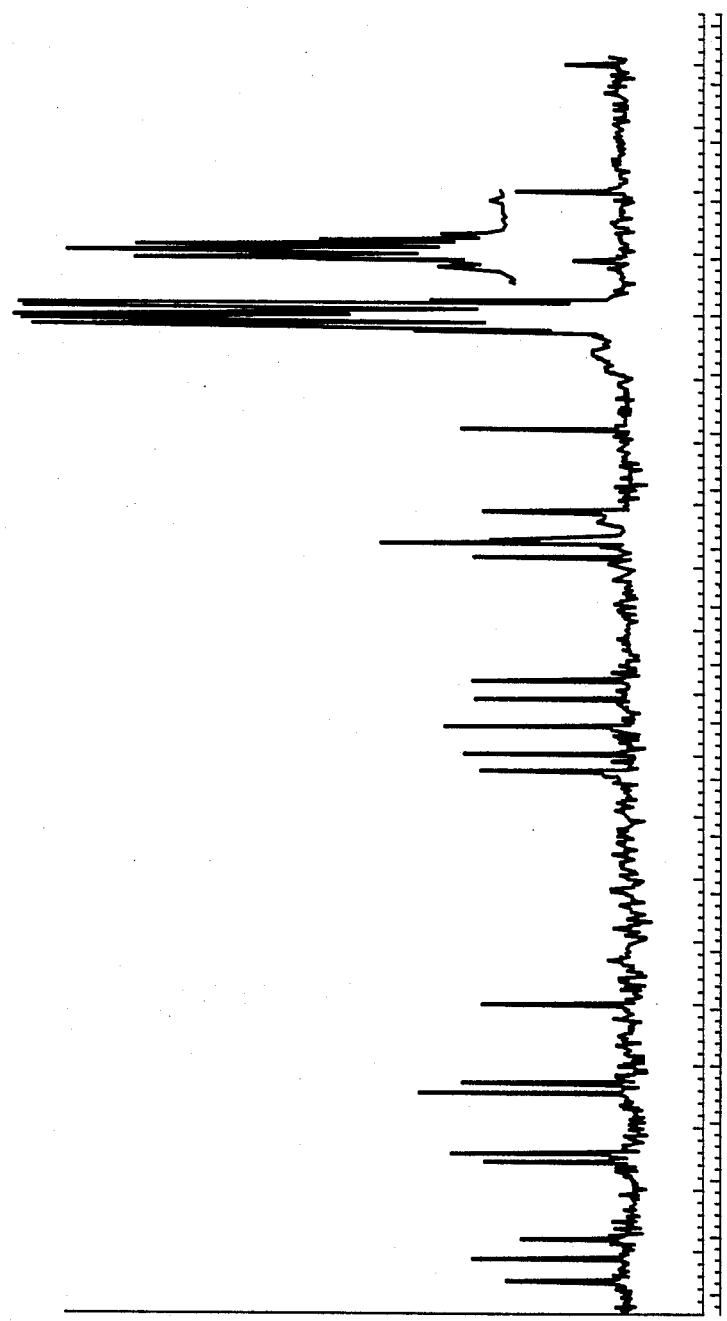
FIG. 3 is the fully-decoupled proton $^{13}$C-NMR spectrum of 7-chloro-4a-hydroxy-8-methoxytetracycline in dimethyl sulfoxide-$d_6$.

(e) The $^1H$— and fully decoupled proton $^{13}C$—NMR spectra in deuterated dimethylsulfoxide(Dmso-$d_6$) are shown in FIGS. 2 and 3, respectively.

Figure 4:
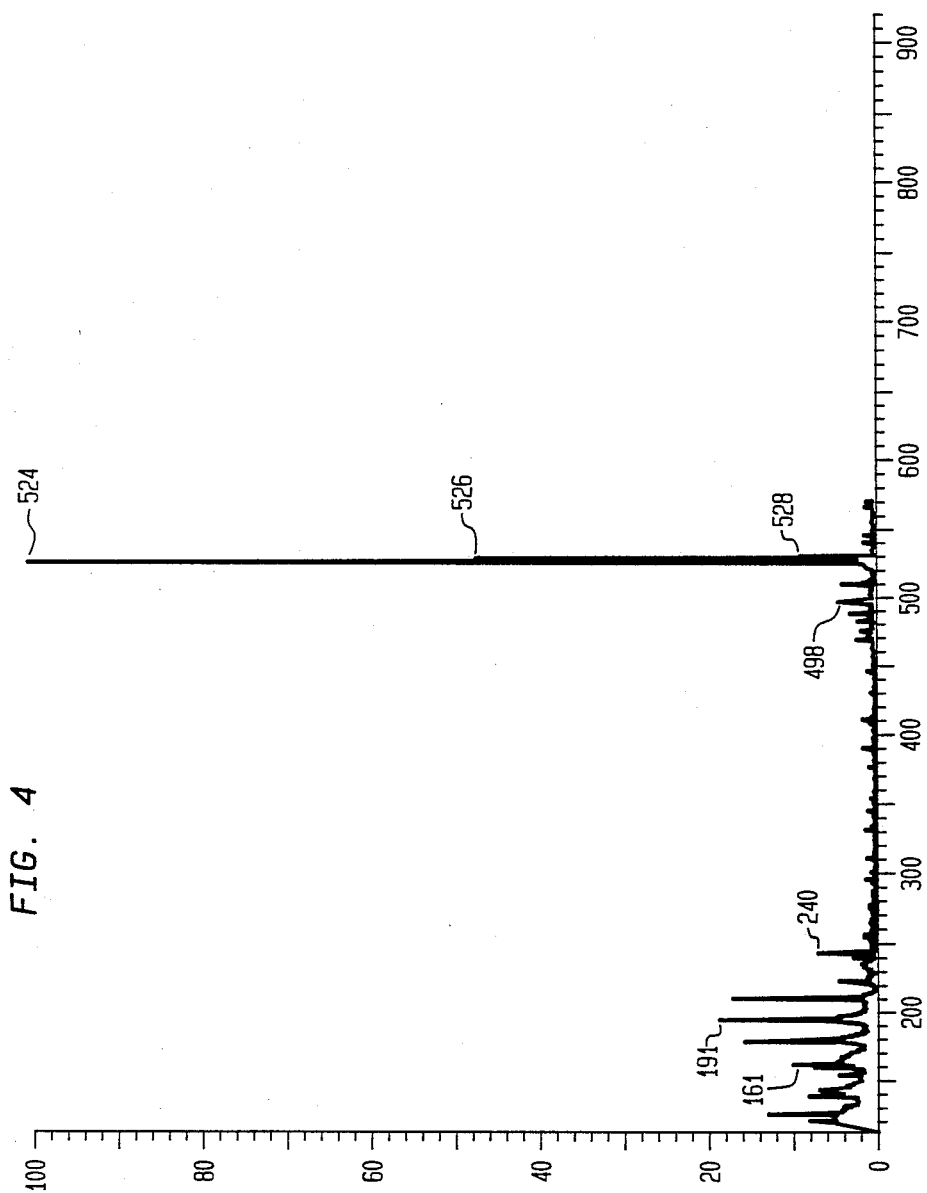
FIG. 4 is the chemical ionization mass spectrum of 7-chloro-4a-hydroxy-8-methoxytetracycline.

(f) The chemical ionization mass spectrum is shown in FIG. 4.

(g) The data from the fully decoupled $^{13}C$—NMR spectra for 7-chloro-8-methoxytetracycline (Compound A), 7-chloro-4a-hydroxy-8-methoxytetracycline (Compound B) and 7-chlorotetracycline are presented in Table II below.

TABLE II $^{13}C$—NMR IN DMSO-$d_6$ FOR 7-CHLORO-8-METHOXY-TETRACYCLINE (COMPOUND A) 7-CHLORO-4a-HYDROXY-8-METHOXYTETRACYCLINE (COMPOUND B) AND 7-CHLOROTETRACYCLINE (COMPOUND C)

| Carbon | Resonance (PPM) | | |
|---|---|---|---|
|  | Compound A) | Compound B | Compound C |
| C-1 | 194.0 | 193.1 | 193.4 |
| C-2 | 95.3 | 96.2 | 95.6 |
| *$CONH_2$ | 171.9 | 172.7 | 172.1 |
| C-3 | 187.3 | 186.4 | 187.3 |
| C-4 | 68.3 | 70.0 | 68.1 |
| $N(CH_3)_2$ | 41.5$^a$ | 40.7$^a$ | 41.0$^a$ |
| C-4a-R | 34.4 (R = H)$^a$ | 76.9 (R = OH)$^a$ | 34.9 (R = H) |
| C-5 | 27.0 | 31.4 | 27.1 |
| C-5a | 42.4$^b$ | 42.3$^b$ | 42.0$^b$ |
| C-6 | 73.4 | 73.0 | 70.4 |
| $CH_3$—C—6 | 20.5 | 20.1 | 25.0 |
| C-6a | 148.5 | 148.6 | 143.6 |
| C-7 | 111.6 | 111.6 | 121.2 |
| C-8 | 163.3 $(OCH_3)^c$ | 163.1 $(OCH_3)^c$ | 139.7 $(H)^c$ |
| C-9 | 100.1 | 100.0 | 118.9 |
| C-10 | 161.9 | 161.6 | 160.7 |
| C-10a | 111.6 | 108.6 | 117.0 |
| C-11 | 190.5 | 189.7 | 193.4 |
| C-11a | 105.6 | 104.3 | 106.1 |
| C-12 | 174.3 | 173.6 | 175.7 |
| C-12a | 73.9 | 73.5 | 73.2 |
| O—$CH_3$ | 57.0 | 56.9. | — |

Based on the above data, the structure of the compound of this invention (without specifying stereochemistry) is the following:

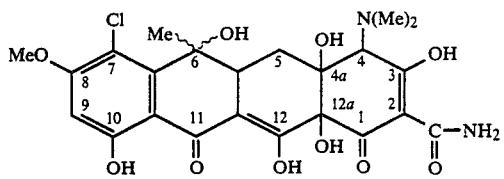

Biological Properties of Antibiotic 7273 Complex and 7-Chloro-4a-Hydroxy-8-Methoxytetracycline The antibiotic 7273 complex containing at least two biologically active components, including 7-chloro-4a-hydroxy-8-methoxytetracycline is active against a variety of gram-positive and gram-negative bacteria when tested in vitro.

In comparative in-vitro antibacterial activity tests using 7-chloro-4a-hydroxy-8-methoxytetracyline and tetracycline performed via conventional microtiter dilution methods in Mueller-Hinton broth, 7-chloro-4a-hydroxy-8-methoxytetracycline showed activity against 91 gram-positive tetracycline-susceptible organisms with a Geometric Mean Minimum Inhibitory Concentration (GMM,mcg/mL) of 1.77 which is similar to the GMM for tetracycline (0.46). The compound of this invention had a GMM of 7.8 against 23 gram-negative tetracycline-susceptible organisms compared to a GMM of 2.3 for tetracycline. The 23 gram-negative organisms included nine strains of *E. coli*, eight of Klebsiella, four of Enterobacter and two of Salmonella. The compound of this invention had a GMM of 5.4 against nine Methicillin-resistant Staphylococci, a GMM of 2.83 against 54 Methicillin-susceptible organisms, a GMM of 0.45 against 25 Streptococci (including Groups A, B, C, G; *S. pneumoniae, S. viridans, S. faecium* and *S. faecalis*), and a GMM of 0.57 against 10 strains of *Bacteroides fragilis* (tested in Mueller-Hinton agar with 5% sheep blood).

In another sequence of comparative in vitro anbibacterial activity tests using 7-chloro-4a-hydroxy-8-methoxytetracycline and an additional component of the antibiotic 7373 complex (hereinafter "additional component") and chlortetracycline, performed via conventional dilution methods in Mueller-Hinton agar, 7-chloro-4a-hydroxy-8-methoxytetracycline and the additional component showed activity against 20 gram-positive chlorotetracycline-susceptive (MIC$\leqq$4) strains, including 2 of *B. subtilis*, 15 of Staphylococcus and 3 of Streptococcus. In 24 hour tests, 7-chloro-4a-hydroxy-8-methoxytetracycline "the compound of this invention" had a GMM of 1.3, compared to a GMM of 0.45 for the additional component and a GMM for chlortetracycline of 0.175. The compound of this invention had a GMM of 58.7 against 8 chlortetracycline-resistant (MIC$\geqq$8) strains including 7 of Staphylococcus and 1 of Streptococcus compared to a GMM of 0.71 for the additional component and a GMM of 20.7 for chlortetracycline. The compound of this invention had a GMM of 3.0 against 22 chlortetracycline-susceptible strains including 8 of *E. coli*, 2 of Enterbacter, 9 of Klebsiella, 1 each of Salmonella, Serratia and Shigella, compared to a GMM of 7.8 for the additional component and a GMM of 3.3 for chlortetracycline. Overall, the additional component was about two-fold less potent than chlortetracycline against both gram-positive and gram-negative chlortetracycline susceptible strains. The additional component was highly active against chlortetracycline-resistant gram-positive strains. The compound of this invention 7-chloro-4a-hydroxy-8-methoxytetracycline had about equal potency as chlortetracycline against chlortetracycline-susceptible gram-negative strains but was about 8 fold less potent than chlortetracycline against chlortetracycline-susceptible gram-positive strains.

The present invention contemplates a method of eliciting an antibacterial effect in a host, e.g., a warm-blooded mammal such as human being having a susceptible bacterial infection, which comprises administering to said host an antibiotically effective amount of 7-chloro-4a-hydroxy-8-methoxytetracycline or a pharmaceutical composition thereof. By the term "eliciting" is meant treating or preventing susceptible bacterial infection.

The methods of this invention are implemented using pharmaceutical compositions comprising a pharmaceutically acceptable carrier and a therapeutically effective quantity of 7-chloro-4a-hydroxy-8-methoxytetracycline or a pharmaceutically acceptable salt thereof.

The preferred pharmaceutically acceptable salts are the acid addition salts. Pharmaceutically acceptable acid addition salts of 7-chloro-4a-hydroxy-8-methoxytetracycline are those formed from strong acids which form acid addition salts containing pharmaceutically acceptable anions, such as hydrochloride, hydrobromide, hydrogen sulfate and trichloroacetate. Acid addition salts may also be formed with carboxylic acids having 2–18 carbon atoms such as aliphatic, cycloaliphatic, aromatic and heterocyclic carboxylic acids, including dicarboxylic acids. Exemplary of such acids are acetic, propionic, stearic, tartaric, maleic, cyclopropylcarboxylic, cyclopentylcarboxylic, adamantioic, furic, nicotinic, thenoic, picolinic, benzoic, phenylacetic and the like.

The antibiotic of this invention may be combined with any suitable pharmaceutical carrier and administered orally, parenterally or topically in a variety of formulations. For oral administration, the antibiotic of this invention may be compounded in the form of tablets, capsules, elixirs or the like. Tablets and capsules may contain such excipients as starch or lactose; liquid oral forms may contain coloring or flavoring agents. Topical preparations may be in the form of creams, hydrophobic and hydrophylic ointments, or aqueous, non-aqueous or emulsion-type lotions. Typical carriers for such formulations are water, oils, greases, polyesters and polyols. Parenteral formulations, e.g., injectable dosage forms, are usually liquids such as solutions or suspensions, with typical carriers being distilled water and saline solution. Oral administration of the compound of this invention or a pharmaceutical composition thereof is preferred.

The dose to be administered in any particular dosage form will be determined by the attending clinician after consideration of various factors, such as the age and condition of the animal species being treated, the susceptibility of the infecting organism to the antibiotic, the stage and severity of the infection.

Generally, the oral dosage administered to humans ranges from about 1.0 mg to about 25 mg per kilogram of body weight per day, in single or divided doses, with about 5 mg per kilogram to about 10 mg per kilogram being preferred.

Generally, the topical dosage administered to humans ranges from about 1% to about 5% antibiotic per day, in single or divided doses, with about 1% to about 3% being preferred.

Generally, the parenteral dosage administered to humans ranges from about 100 mg to about 2000 mg per day in single or divided doses, with about 500 mg to about 1000 mg being preferred.

In treating certain patients with the compounds of this invention, it is possible to include other pharmaceutically active ingredients in the same dosage unit.

THE MICROORGANISM

The microorganism used for the production of antibiotic 7273 complex is a biologically pure culture of *Dactylosporangium vescum* ATCC 39499.

A culture of this microorganism has been made a part of the collection of the American Type Culture Collection (ATCC) in Rockville, Md. where it has been assigned accession number ATCC 39499. Subcultures of *Dactylosporangium vescum* ATCC 39499 are available to the public without restriction. Use of the microorganism is dependent on U.S. Patent Laws.

The microorganism was isolated from a sample of soil collected in the Kasie Valley of Zambia. It had been characterized and found to have the microscopic, macroscopic, and whole cell hydrolysis properties of the genus Dactylosporangium.

Description of the Producing Strain:
Dactylosporangium vescum sp. nov. ATCC 39499

The taxonomic methods used herein are those cited by R. E. Gordon and V. Blanchard, "Some criteria for the recognition of *Nocardia madura*", *J. Gen. Microbiol.*, 45, pp 355–364 (1966); by Luedemann and Brodsky, in "*Micromonospora carbonacea* sp. nov., an everninomicin-producing organism", Antimicrob Agents Chemotherapy, p 47–52, 1964; by Horan and Brodsky, in an article in *International Journal Syst. Bacterial.*, Vol. 32, p 195–200, 1982 entitled "A Novel Antibiotic-Producing Actinomadura, *Actinomadura kijaniata* sp. nov."; by Becker et al, in an article in *Applied Microbiology*, Vol. 13, p 236–243, 1966 entitled "Chemical Composition of Cell Wall Preparations from Strains of Various Genera of Aerobic Actinomycetes"; by Lechevalier and Lechevalier, in an article in *International Journal Syst. Bacterial.*, Vol. 20, p 487–493, 1970 entitled "Chemical Composition as a Criterion in the Classification of Aerobic Actinomycetes; by Shirling and Gottlieb, in an article in *International Journal Syst. Bacteriol*, Vol. 16, p 313–340, 1966 entitled "Methods for Characterization of Streptomyces Species; and by Waksman, in *The Actinomycetes* Vol. 2, (The Williams & Wilkins Co., Baltimore, Md., 1961).

TABLE III

Macroscopic and Microscopic Characteristics of *Dactylosporangium vescum* ATCC 39499

| Macroscopic | Microscopic |
|---|---|
| Aerial Mycelia are not formed | |
| Good growth occurs after 14–21 days at 30° C. on Emerson's Agar, yeast extract glucose agar, yeast extract-malt extract agar and peptone iron agar. On most other media, fair growth is observed. Rudimentary aerial mycelia are formed on tomato paste-oatmeal agar and a bright yellow | Abundant, large sporangioles about 2.0 microns in diameter, are formed along the length of fine (0.5–0.6 micron) vegetative hyphae after 5 days on water agar at 30° C. The sporangioles occur singly or on short sporophores and are readily formed in broth. Finger-like sporangia, |

TABLE III-continued
Macroscopic and Microscopic Characteristics of Dactylosporangium vescum ATCC 39499

| Macroscopic | Microscopic |
|---|---|
| diffusible pigment is produced on Bennett's Agar. The color of vegetative mycelial pigments usually ranges from tan to yellow to orange. | 1.0–1.2 microns in diameter by 4.0 to 6.0 microns in length, occuring in clusters, are sparingly formed on water agar at 30° C. Each sporangium contains 3 to 4 spores. Upon wetting the sporangia dehisce to release motile spores. |

The culture characteristics of the microorganism *Dactylosporangium vescum* ATCC 39499 on various standard media are reported in Table IV. In the description of the growth characteristics of the microorganism in Table IV, two color designators are employed. The first is a color name taken from the "Descriptive Color Name Dictionary" by Taylor, Knoche and Granville published by the Container Corporation of America (1950) U.S.A., with a color chip number corresponding to the color name, the chip number being taken from "The Color Harmony Manual,: 4th Edition, 1958, also published by the Container Corporation of America. The second designator consists of a color name and number which refers to the synonym and near synonym found in the National Bureau of Standards, Circular 553, Nov. 1, 1965 (U.S.A.).

Growth of the microorganism, *Dactylosporangium vescum* ATCC 39499 on various carbon compounds is reported in Table V.

Physiologic characteristics of the microorganism *Dactylosporangium vescum* ATCC 39499 are reported in Table VI.

A comparison of the characteristics of *Dactylosporangium vescum* ATCC 39499 with those of other species of Dactylosporangium is listed in Table VII.

Whole cell analysis of the microorganism *Dactylosporangium vescum* ATCC 39499 found hydroxydiaminopimelic acid as the characteristic cell wall amino acid, and arabinose and xylose as the characteristic whole cell sugars.

Growth of the microorganism occurs from 27° to 40° C. on yeast-dextrose agar. Poor growth occurs above about 40° C., with optimum growth at from 27° to 35° C.

TABLE IV
Macroscopic Appearance of Dactylosporangium vescum ATCC 39499 on Various Descriptive Media[a,b]

| Medium | Description |
|---|---|
| Bennett's Agar | G: Fair |
| | S: Flat |
| | AM: Absent |
| | DFP: Present; yellow brown |
| | C: g 2ie, light mustard tan |
| Czapek Sucrose Agar | G: Fair |
| | S: Flat |
| | AM: Absent |
| | DFP: Absent |
| | C: g 3ia, bright melon yellow |
| Glucose Asparagine Agar | G: Fair |
| | S: Flat |
| | AM: Absent |
| | DFP: Absent |
| | C: g 3ia, bright mellon yellow |
| Glycerol Asparagine Agar | G: Fair |
| | S: Flat |
| | AM: Absent |
| | DFP: Absent |
| | C: g 41c, dusty orange |
| Nutrient Agar | G: Fair to poor |
| | S: Flat |
| | AM: Absent |
| | DFP: Absent |
| | C: g 3le, cinnamon |
| Peptone Glucose Agar | G: Poor |
| | S: non- |
| | AM: descript. |
| | DFP: |
| | C: |
| Potato Dextrose Agar | G: Fair |
| | S: Raised, granular |
| | AM: Absent |
| | DFP: Absent |
| | C: g 4nc, russet orange |
| Emerson's Agar | G: Good |
| | S: Raised, folded |
| | AM: Absent |
| | DFP: Absent |
| | C: g 4ng, light brown |
| N—Z—Amine Glucose Agar | G: Moderate |
| | S: Raised, folded |
| | AM: Absent |
| | DFP: Absent |
| | C: g 41c, dusty orange |
| Yeast Extract Glucose Agar | G: Good |
| | S: Raised, granular |
| | AM: Absent |
| | DFP: Absent |
| | C: g 4nc, russet orange |
| Tomato Paste-Oatmeal Agar | G: Moderate |
| | S: Raised, folded |
| | AM: Bloom, white |
| | DFP: Absent |
| | C: g 41c, dusty orange |
| Yeast Extract Malt Extract Agar (ISP #2) | G: Good |
| | S: Raised, folded |
| | AM: Absent |
| | DFP: Absent |
| | C: g 3ic, light amber |
| Oatmeal Agar (ISP #3) | G: Fair |
| | S: Flat |
| | AM: Absent |
| | DFP: Absent |
| | C: g 3ga, melon yellow |
| Inorganic Salts-Starch Agar (ISP #4) | G: Moderate |
| | S: Raised, folded |
| | AM: Absent |
| | DFP: Absent |
| | C: g 4na, bright orange |
| Starch Agar (W #21) | G: Fair |
| | S: Flat |
| | AM: Absent |
| | DFP: Absent |
| | C: g 3lc, amber |
| Calcium Maleate Agar (W #7) | G: Fair |
| | S: Flat |
| | AM: Absent |
| | DFP: Absent |
| | C: g 4la, orange |
| Calcium Citrate Agar | G: Fair |
| | S: Flat to raised |
| | AM: Absent |
| | DFP: Absent |
| | C: g 4la, orange |
| Peptone Iron Agar (ISP #6) | G: Good |
| | S: Raised, folded |
| | AM: Absent |
| | DFP: Absent |
| | C: g 4ne, luggage tan |
| Tyrosine Yeast Extract Agar | G: Good |
| | S: Raised |
| | AM: Absent |
| | DFP: Absent |
| | C: g 4pe, orange rust |
| Starch Yeast Agar | G: Moderate |

TABLE IV-continued

Macroscopic Appearance of *Dactylosporangium vescum* ATCC 39499 on Various Descriptive Media[a,b]

| Medium | Description |
|---|---|
| | S: Flat, folded |
| | AM: Absent |
| | DFP: Absent |
| | C: g 4pe, orange rust |

[a]Observations made after 14–21 days at 30° C.
[b]G = Growth; S = Surface Characteristics; AM = Aerial Mycelia; DFP = Diffusible Pigments; and C = Color

TABLE V

Carbohydrate utilization[1] of *Dactylosporangium vescum* ATCC 39499

| Utilization of: | Result |
|---|---|
| Adonitol | −, Poor |
| D-Arabinose | +, Fair |
| L-Arabinose | ++, Moderate |
| Cellibiose | ++, Moderate |
| Dextrin | ++, Moderate |
| Dulcitol | −, Poor |
| Erythritol | −, Poor |
| Fructose | ++, Moderate |
| Galactose | ++, Moderate |
| Glucose | +++, Good |
| α-m-d-glucoside | −, Poor |
| Glycerol | ++, Moderate |
| Inositol | −, Poor |
| Inulin | +, Fair |
| Lactose | ++, Moderate |
| Maltose | +++, Good |
| Mannitol | +++, Good |
| Mannose | +++, Good |
| Melibiose | +, Fair |
| Melizitose | −, Poor |
| Raffinose | −, Poor |
| Rhamnose | ++, Moderate |
| Ribose | −, Poor |
| Sucrose | +++, Good |
| Trehalose | +++, Good |
| D-Xylose | ++, Moderate |

[1]Medium of Luedemann and Brodsky (Antimicrob. Ag. Chemoth. 1965)

TABLE VI

Physiologic Characteristics of *Dactylosporangium vescum* ATCC 39499

| Test | Result |
|---|---|
| Growth in the Presence of 50 mcg/mL | |
| Gentamicin | + |
| Sisomicin | − |
| Neomycin | − |
| Kanamycin | − |
| Rosaramicin | + |
| Erythromycin | − |
| Lincomycin | + |
| Clindamycin | + |
| Tetracycline | + |
| Penicillin G | − |
| Cephalothin | − |
| Rifamycin | − |
| Everninomicin | − |
| Novobiocin | − |
| Spectinomycin | − |
| Hydrolysis of | |
| Adenine | − |
| Hypoxanthine | − |
| Tyrosine | − |
| Xanthine | − |
| Xylan | + |
| Casein | + |
| Gelatin | + |
| Hippurate | + |
| Esculin | + |
| Breakdown of | |
| Urea | − |
| Allantoin | − |
| Loefflers Serum | − |
| Dorset's Egg | − |
| Nitrate to Nitrite | + |
| Growth at | |
| 27° C. | ++, Moderate |
| 35° C. | +++, Good |
| 40° C. | ++, Moderate |
| 45° C. | ±, Poor |
| Survival | |
| 50° C./8 hr. | + |
| Growth in the Presence of NaCl | |
| 1% | +++, Good |
| 2% | ++, Moderate |
| 3% | ++, Moderate |
| 4% | ±, Poor |
| Formation of | |
| H$_2$S | − |
| Melanin | − |

Results reported in Tables V and VI are expressed as + (positive) and − (negative).

TABLE VII

Differentiating Characteristics of Species of Dactylosporangium

| Organism | Vegetative mycelial pigments | Formation of Sporangioles |
|---|---|---|
| *Dactylosporangium vescum* ATCC 39499 | tan to yellow to orange | abundant |
| *D. aurantiacum* ATCC 23491 | hyaline to orange | present |
| *D. matsuzakiense* ATCC 31570 | orange | not observed |
| *D. roseum* IFO 14352 | orange to rose red | not observed |
| *D. salmoneum* ATCC 31222 | cream to salmon | present |
| *D. thailandense* ATCC 23490 | orange to reddish brown | present |
| *D. variesporum* ATCC 31203 | orange to light reddish brown | present |
| *D. vianceum* ATCC 35207 | wine to ebony brown | present |

| Organism | Diffusible Pigments | Utilization of Glycerol | Utilization of Rhamnose | Growth on 3% NaCl |
|---|---|---|---|---|
| *Dactylosporangium vescum* ATCC 39499 | yellow-brown | + | + | + |
| *D. aurantiacum* ATCC 23491 | none | − | + | + |
| *D. matsuzakiense* ATCC 31570 | light brownish pink, rarely | − | + | − |
| *D. roseum* IFO 14352 | none | − | − | + |
| *D. salmoneum* ATCC 31222 | none | + | + | − |
| *D. thailandense* ATCC 23490 | light orange to light brown | − | + | − |
| *D. variesporum* ATCC 31203 | reddish orange | + | − | − |
| *D. vianceum* ATCC 35207 | wine to deep red | − | + | + |

Based on the formation of finger-like sporangia each containing a single row of two to four motile spores, abundant formation of sporangioles both on agar and in broth, the presence of hydroxydiaminopimelic acid in the cell wall and xylose and arabinose in hydrolyzed whole cells the organism is identified as a member of the genus Dactylosporangium.

Physiologic characteristics differentiating *D. vescum* ATCC 39499 from the described species of Dactylosporangium are presented in Table VII. None of the species of Dactylosporangium share with *D. vescum* the combination of tan to yellow vegetative mycelial pigments, abundant and rapid formation of sporangioles, formation of yellow diffusible pigments, utilization of glycerol and rhamnose, ability to grow in the presence of 3% NaCl and the production of the novel 8-methoxy-4a-hydroxy-7-chlortetracycline.

Strain ATCC 39499 is therefore considered to be a distinct, new species of Dactylosporangium designated *D. vescum* (Theimann, Pagani and Beretta) Horan and Brodsky sp. nov., and this strain is the type strain of the new species.

It is understood that in accordance with the rules of Nomenclature of Bacteria (S. P. Lapage et al. Ed. 1975, *International Code of Nomenclature of Bacteria,* 1976 revision) *D. vescum* is the type strain and that should another strain be found, the type strain would also be the type subspecies.

FERMENTATION OF THE MICROORGANISM

Antibiotic 7273 complex is produced when the elaborating microorganism, *Dactylosporangium vescum,* is grown in an aqueous nutrient medium under submerged aerobic conditions at a temperature of about 27° C. to 40° C., preferably at from 27° C. to 35° C., and at a pH of from about 6.5 to 8.0 with agitation until substantial antibiotic activity is imparted to the medium. Temperature studies indicate that the organism grows rapidly at 30° C. Therefore, the fermentation is preferably conducted employing a single temperature pattern of 30° C. for the first 48 hours as well as for the period 24 to 96 hours. The fermentation is generally conducted from 65 to 96 hours although preferably for 66 hours. To determine when peak antibiotic production has been reached, samples of the medium were assayed every 24 hours (starting at 48 hrs.) for antibiotic content by bioassay of the whole broth against *S. aureus* ATCC 209P (pH 8.0) and *E. coli* ATCC 10536 (pH 8.0). The growth of the organism (packed cell volume), pH and dissolved oxygen levels are determined either intermittantly or continuously.

As nutrient medium, there is employed any suitable medium containing a source of carbon, for example an assimilable carbohydrate, and a source of nitrogen, for example an assimilable nitrogenous or proteinaceous material.

The medium employed for the fermentation contained NZ-Amine A (an enzymatic hydrolysate of casein) and soluble starch as the major sources of nitrogen and carbon. Under these conditions, the microorganism produced antibiotic 7273 complex containing at least 2 biologically active components as determined by bioautography against both *S. aureus* and *E. coli* of the complex after development of a thin layer chromatography plate in 2:2:1 (v/v/v) chlorofrom:methanol:pH 3.5 acetate buffer.

The foregoing media are exemplary of the nutrients utilized by *Dactylosporangium vescum* to produce antibiotic 7273 complex. However, it is obvious to those skilled in the fermentation art that a wide range of nutrients obtained from a number of suppliers may be substituted for the foregoing, and that generally good growth and antibiotic production can be obtained, such nutrients being the functional equivalent to those set forth herein.

The fermentation is generally conducted by initially sterilizing the fermentation medium prior to the addition of the inoculum.

The pH of the fermentation medium is generally maintained at from 6.5 to 8.0, a pH of from 6.5 to 7.5 being preferred. Prior to sterilization, the pH of the medium is usually adjusted to 6.7 and prior to inoculation, the pH is usually adjusted to 7.0.

The fermentation was initiated by addition of the inoculum to the broth. Generally, inoculum volume is 2.5% of total broth volume. The inoculum is prepared by addition of a sample of the frozen whole broth to an appropriate medium. A particularly preferred medium comprises beef extract, 0.3%; tryptone, 0.5; cerelose, 0.1%; potato starch, 2.4%; yeast extract, 0.5%; and calcium carbonate, 0.2%. The pH of the inoculum medium is adjusted to 7.5 prior to sterilization. The inoculum stage of the fermentation usually requires from 24 to 120 hours with 1 to 2 days preferred and is generally conducted at about 30° C. with agitation. Agitation and a positive air flow, generally about 3.5 L/min. are employed during the fermentation.

EXAMPLE 1

Preparation of Antibiotic 7273 Complex

A. Inoculum Preparation (1) Initial Stage

Prepare a 300 mL Erlenmeyer flask with 70 mL of the following germination medium:

| | |
|---|---|
| Beef Extract | 3 g |
| Tryptone | 5 g |
| Yeast Extract | 5 g |
| Cerelose | 1 g |
| Potato Starch | 24 g |
| Calcium Carbonate | 2 g |
| Tap Water | 1000 mL |
| AF-1 | 1 mL |

AF-1 is an antifoam agent available from Dow Corning Corp., Midland, MI 48641.

Adjust the pH of the germination broth to 7.5. Sterilize the broth and after cooling add 3.5 mL of a frozen whole broth sample of the microorganism of this invention from a previously prepared inoculum to each flask broth. Incubate at 30° C. with continual agitation at 300 rpm for 48 hours.

(2) Second Stage

Transfer 25 mL of the first stage germination broth to each of twenty 2-liter Erlenmeyer flasks, each containing 500 mL of the same germination medium and which had been previously pH adjusted and sterilized. Incubate at 30° C. with continual agitation at 300 rpm for 48 hours.

B. Fermentation

In a 14 L fermentor, add 11 L of the following medium:

| | |
|---|---|
| Yeast Extract | 5 g |
| Casein Hydrolysate | 5 g |
| Cerelose | 10 g |
| Soluble Starch | 20 g |
| Calcium Carbonate | 4 g |
| Cobalt (II) Chloride ($10^{-3}$M) | 1 mL |
| AF-1 | 1 mL |
| $MgCl_2.6H_2O$ | 0.5 g |

| | |
|---|---|
| -continued | |
| Tap water | 1000 mL |

Adjust the pH of the medium to 6.7 and then sterilize the medium. After sterilization, adjust the pH of the medium to 7.0 with a sterile alkaline solution. Inoculate the fermentation medium with 5% volume of the second stage inoculum preparation of Step A. Incubate the fermentation mixture at 30° C. with 0.35 VVM (3.5 L/min) of air flow and 350 rpm agitation for about 66 hours.

C. Isolation

Adjust the pH of the whole fermentation broth of step B to 4 with 6N $H_2SO_4$. Extract 80 L of the whole broth four times with equal volumes of ethyl acetate. Combine the ethyl acetate solutions, dry them over anhydrous sodium sulfate and remove the solvent by stripping to give a residue. Dissolve the residue in 500 mL of acetone and then add 56 L of a 1:4 (v/v) mixture of ethyl ether:hexane until a precipitate results. Filter the precipitate and dry in a vacuum to give the antibiotic 7273 complex.

EXAMPLE 2

Separation of Antibiotic 7273 Complex-Isolation of 7-chloro-4a-hydroxy-8-methoxytetracycline Suspend 12.5 g of the crude antibiotic 7273 complex from Example 1C in 100 mL of $H_2O$ and adjust the pH to 1.5 with 5% HCl and filter. Add 10 g of ethylenediaminetetracetic acid to the filtrate and adjust the pH of the filtrate to 6.0 with concentrated ammonium hydroxide. Extract the aqueous phase so formed four times with equal volumes of methylene chloride. Separate, combine and dry the organic phase over anhydrous sodium sulfate. Remove the methylene chloride to give 3.9 g of purified antibiotic 7273 complex. Adsorb a solution of 3.9 g of the purified complex in 30 mL of 0.02N HCl on a 7.62 cm (id)×101.6 cm (h) chromatography column containing 300 mL of Sephadex G-25 filtration gel (medium; dry particles size 50-150 μm). (Sephadex G-25 is a cross-linked dextran, a polysaccharide, available from Pharmacia Fine Chemicals, Inc. Piscataway, N.J.). Elute the column with 0.02N HCl at a flow rate of about 1 mL per minute. Monitor the activity of each fraction 10 mL) against *S. aureus* ATCC 209P (pH 8.0) and *E. coli* ATCC 10536 (pH 8.0) using a disc diffusion assay. Spot the active fraction on thin layer chromatography plates developed in a 2:2:1 (v/v/v) chloroform:methanol:pH 3.5 acetate buffer. Detect the antibiotic components by bioautography against both *S. aureus* and *E. coli*

The additional component was isolated using similar conditions to those described above. Monitor the activity of the Sephadex G-25 column as described above to obtain the additional component.

Obtain the novel 7-chloro-4a-hydroxy-8-methoxytetracycline by combining the desired fractions. Lyophilize the pooled desired fractions to provide the title compound as a yellow powder having physico-chemical data summarized in Table I.

Formulations

EXAMPLE 3

Parenteral Formulation

Per vial: 7-chloro-4a-hydroxy-8-methoxytetracycline (hereinafter "drug") as a sterile powder. Unit dosages, maybe 100 mg, 200 mg, 500 mg, 1 g and 2 g. Add sterile water for injection U.S.P. or bacteriostatic water for injection U.S.P., for reconstitution.

EXAMPLE 4

Capsule Formulation

| Item No. | Ingredient | mg/capsule | mg/capsule |
|---|---|---|---|
| 1 | Drug | 100 | 200 |
| 2 | Lactose | 122 | 244 |
| 3 | Corn Starch, Dried | 22.5 | 51 |
| 4 | Magnesium Stearate | 2.5 | 5 |
| | | 250 mg | 500 mg |

Method

Mix Item Nos. 1, 2, and 3 in a suitable mixer for 10-15 minutes. Add Item No. 4 and mix for 1-3 minutes. Fill the above mixture in two-piece hard gelatin capsules of required size.

EXAMPLE 5

Tablet Formulation

| Item No. | Ingredient | mg/capsule | mg/capsule |
|---|---|---|---|
| 1 | Drug | 125 | 250 |
| 2 | Lactose | 93.75 | 187.5 |
| 3 | Corn Starch, as a 10% paste | 5 | 10 |
| 4 | Corn Starch, Dried | 25 | 50 |
| 5 | Magnesium Stearate | 1.25 | 2.5 |
| | | 250 mg | 500 mg |

Method

Mix Item Nos. 1, 2 and a portion of Item No. 4 in a suitable mixer for 10-15 minutes. Granulate the mixture with Item No. 3. Pass the wet granulation through a course screen (e.g., ¼") if needed, and then dry the wet granules. Mill the dried granules using a suitable milling machine. Add Item No. 5 and the remaining amount of Item No. 4 with the dried granules in a suitable blender. Mix for 10-15 minutes. Compress the mixture into the tablets of required shape and size on a suitable tablet machine. The tablets may be coated using standard coating procedures.

EXAMPLE 6

Topical Formulation

| Item No. | Ingredient | mg/g |
|---|---|---|
| 1 | Drug | 25 |
| 2 | Ethyl Alcohol | 400 |
| 3 | Hydroxypropyl Cellulose | 15 |
| 4 | Polyethylene Glycol 400 | 560 |

Mix Item Nos. 1, 2 and 4 in a suitable mixer. Stir vigorously and charge Item No. 3. Maintain stirring until uniformity is achieved.

EXAMPLE 7

Oral Powder for Reconstitution (I)

Part A (Powder Formulation)

| Item No. | Ingredient | mg/g |
|---|---|---|
| 1 | Drug | 46.3 |
| 2 | Flavor(s) | q.s. |
| 3 | Colorant | q.s. |
| 4 | Preservative | q.s. |
| 5 | Buffer Agents | q.s. |
| 6 | Sugar | q.s. |
|   | To make | 1.0 g |

Mix Item Nos. 1, 2, 3, 4 and 5 thoroughly. Charge Item No. 6 and mix until uniformity is achieved.

Part B (Reconstitution)

Charge 54 g of above formulated powder into a proper container and add enough water to make up 100 ml. Shake well after the addition of water. Each 5 ml (1 teaspoonful) will then contain drug equivalent to 125 mg.

EXAMPLE 8

Oral Powder for Reconstitution (II)

Part A (Powder Formulation)

| Item No. | Ingredient | mg/g |
|---|---|---|
| 1 | Drug | 416.7 |
| 2 | Flavor(s) | q.s. |
| 3 | Colorant | q.s. |
| 4 | Preservative | q.s. |
| 5 | Buffering Agents | 28.3 |
| 6 | Saccharin | q.s. |
| 7 | PVP |  |
|   | To make | 1.0 g |

Mix Item Nos. 1, 2, 3, 4, 5, 6, and 7 well until uniform.

Part B (Reconstitution

Charge 6.0 g of above powder into a suitable container and add enough water to make up 100 ml. Shake well until uniform. Each 5 ml will then contain drug equivalent to 125 mg.

EXAMPLE 9

Oral Liquid

| Item No. | Ingredient | mg/ml |
|---|---|---|
| 1 | Drug | 25.0 |
| 2 | Sweetner | q.s. |
| 3 | Flavor | q.s. |
| 4 | Colorant | q.s. |
| 5 | Vegetable Oil | q.s. |
|   | To make | 1.0 ml |

Charge 90% of Item No. 5 needed into a suitable container. Charge Item Nos. 1, 2, 3 and 4 and mix well. Bring to the final volume by the reserved Item No. 5.

EXAMPLE 10

Suppository

| Item No. | Ingredient | Suppository |
|---|---|---|
| 1 | Drug | 125.0 |
| 2 | Witepsol H-15 | 1868 |

Melt Item No. 2 and blend Item No. 1 until uniform. Pour into mold and congeal in refrigerator. Remove suppository from mold.

We claim:

1. The substantially chemically pure compound represented by the formula

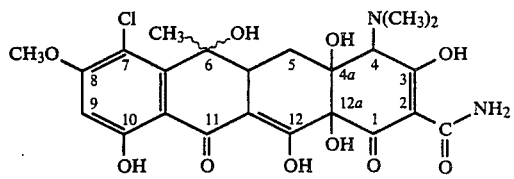

or a pharmaceutically acceptable salt thereof.

2. A pharmaceutical composition comprising an antibiotically effective amount of the compound of claim 1 and a pharmaceutically acceptable carrier or diluent.

3. A pharmaceutical composition of claim 2 suitable for parenteral administration.

4. A pharmaceutical composition of claim 2 suitable for topical administration.

5. A pharmaceutical composition of claim 2 suitable for oral administration.

6. A method of eliciting an antibiotic effect in a host having a susceptible infection which comprises administering to said host an antibiotically effective amount of the compound of claim 1 or a pharmaceutical composition thereof.

7. A method of claim 6 wherein the route of administration is parenteral.

8. A method of claim 6 wherein the route of administration is topical.

9. A method of claim 6 wherein the route of administration is oral.

* * * * *